United States Patent
Talish et al.

(10) Patent No.: US 6,932,308 B2
(45) Date of Patent: Aug. 23, 2005

(54) TRANSDUCER MOUNTING ASSEMBLY

(75) Inventors: Roger J. Talish, Hillsborough, NJ (US); Kenneth J. Urgovitch, Clifton, NJ (US); Donald E. Krompasick, Bethlehem, PA (US); Anthony James, Bartlett, TN (US); Wayne Rankhorn, Rossville, TN (US); Kevin Tanis, Pompton Lakes, NJ (US); Robert Scott Ludecker, Freeport, NY (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 10/029,095

(22) Filed: Oct. 25, 2001

(65) Prior Publication Data

US 2002/0145091 A1 Oct. 10, 2002

Related U.S. Application Data

(60) Provisional application No. 60/242,994, filed on Oct. 25, 2000.

(51) Int. Cl.$^7$ .............................................. F21V 35/00
(52) U.S. Cl. ................... 248/226.11; 248/314; 600/439
(58) Field of Search ....................... 248/226.11, 226.12, 248/314; 601/2–4, 34; 600/439

(56) References Cited

U.S. PATENT DOCUMENTS

| | | | | |
|---|---|---|---|---|
| 1,604,870 A | * | 10/1926 | Asman | ................... 248/225.11 |
| 3,134,451 A | | 5/1964 | Hanssen | |
| 3,193,034 A | | 7/1965 | Hutchinson et al. | |
| 3,304,036 A | * | 2/1967 | Davis | ................... 248/225.11 |
| 3,310,049 A | | 3/1967 | Clynes | |
| 3,433,663 A | | 3/1969 | Underwood | |
| 3,499,437 A | | 3/1970 | Balamuth | |
| 3,550,586 A | | 12/1970 | Balamuth | |
| 3,594,993 A | | 7/1971 | Heyse | |
| 3,701,352 A | | 10/1972 | Bosworth | |
| 3,760,799 A | | 9/1973 | Crowson | |
| 3,767,195 A | | 10/1973 | Dimick | |
| 3,828,769 A | | 8/1974 | Mettler | |
| 3,855,638 A | | 12/1974 | Pilliar | |
| 3,961,380 A | | 6/1976 | Garr | |
| 3,986,212 A | | 10/1976 | Sauer | |
| 4,037,592 A | * | 7/1977 | Kronner | ................ 128/660.03 |
| 4,105,017 A | | 8/1978 | Ryaby et al. | |
| 4,108,165 A | * | 8/1978 | Kopp et al. | ............ 128/660.03 |
| 4,127,125 A | | 11/1978 | Takemoto et al. | |

(Continued)

FOREIGN PATENT DOCUMENTS

| | | |
|---|---|---|
| AU | 19950292 | 2/2000 |
| CA | 1328485 | 4/1994 |
| DE | 3639263 A1 | 6/1987 |
| DE | 4111055 A1 | 10/1991 |
| DE | 19613425 | 1/1997 |

(Continued)

OTHER PUBLICATIONS

Cass, "Fabrication of Continuous Ceramic Fiber by the Viscous Suspension Spinning Process," *Ceramic Bulletin*, vol. 70, No. 3, pp. 424–429 (1991).

Clarke, P.R. et al., "Physical and Chemical Aspects of Ultrasonic Disruption of Cells", *JASA* (1969), 47(2): 649–653.

Hill, C.R., "Ultrasonic Exposure Thresholds for Changes in Cells and Tissues", *JASA* (1972), 52(2): 667–672.

(Continued)

*Primary Examiner*—Korie Chan
(74) *Attorney, Agent, or Firm*—Kilpatrick Stockton LLP

(57) ABSTRACT

An apparatus for adjustably securing an ultrasonic transducer to an orthopedic appliance is disclosed. The apparatus having; (a) an optional adjustable clamp adapted to adjustably secure the apparatus to an element of an orthopedic appliance; (b) a transducer holder adapted to secure the transducer to the apparatus; (c) an adjustable connector adapted to adjustably connect the optional adjustable clamp to the transducer holder.

4 Claims, 7 Drawing Sheets

U.S. PATENT DOCUMENTS

| | | |
|---|---|---|
| 4,164,794 A | 8/1979 | Spector et al. |
| 4,170,045 A | 10/1979 | Estes |
| 4,176,664 A | 12/1979 | Talish |
| 4,206,516 A | 6/1980 | Pilliar |
| 4,216,766 A | 8/1980 | Duykers et al. |
| 4,227,111 A | 10/1980 | Cross et al. |
| 4,233,477 A | 11/1980 | Rice et al. |
| 4,269,797 A | 5/1981 | Mikiya et al. |
| 4,296,753 A | 10/1981 | Goudin |
| 4,312,536 A | 1/1982 | Lloyd |
| 4,315,503 A | 2/1982 | Ryaby et al. |
| 4,351,069 A | 9/1982 | Ballintyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Bhagat et al. |
| 4,421,119 A | 12/1983 | Pratt, Jr. |
| 4,431,038 A * | 2/1984 | Rome .................. 248/314 |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,476,847 A | 10/1984 | Taenzer et al. |
| 4,476,874 A | 10/1984 | Taenzer et al. |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish |
| 4,556,066 A | 12/1985 | Semrow |
| 4,570,640 A | 2/1986 | Barsa |
| 4,573,996 A | 3/1986 | Kwiatek et al. |
| 4,594,662 A | 6/1986 | Devaney |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,669,483 A * | 6/1987 | Hepp et al. ............ 128/660.03 |
| 4,677,438 A | 6/1987 | Michiguchi et al. |
| 4,687,195 A | 8/1987 | Potts |
| 4,708,127 A | 11/1987 | Abdelghani |
| 4,710,655 A | 12/1987 | Masaki |
| 4,726,099 A | 2/1988 | Card |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,926,870 A | 5/1990 | Brandenburger |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | Fallin |
| 5,133,420 A | 7/1992 | Smith |
| 5,134,999 A | 8/1992 | Osipov |
| 5,139,498 A | 8/1992 | Astudillo Ley |
| 5,140,988 A | 8/1992 | Stouffer et al. |
| 5,143,069 A | 9/1992 | Kwon et al. |
| 5,143,073 A | 9/1992 | Dory |
| 5,163,598 A | 11/1992 | Peters et al. |
| 5,172,692 A | 12/1992 | Kulow et al. |
| 5,178,134 A | 1/1993 | Vago |
| 5,181,512 A | 1/1993 | Viebach et al. |
| 5,184,605 A | 2/1993 | Grzeszykowski |
| 5,186,162 A | 2/1993 | Talish et al. |
| 5,191,880 A | 3/1993 | McLeod et al. |
| 5,197,475 A | 3/1993 | Antich et al. |
| 5,201,766 A | 4/1993 | Georgette |
| 5,209,221 A | 5/1993 | Riedlinger |
| 5,211,160 A | 5/1993 | Talish et al. |
| 5,230,334 A | 7/1993 | Klopotek |
| 5,230,345 A | 7/1993 | Curran et al. |
| 5,230,921 A | 7/1993 | Waltonen et al. |
| 5,235,981 A | 8/1993 | Hascoet et al. |
| 5,254,123 A | 10/1993 | Bushey |
| 5,259,384 A | 11/1993 | Kaufman et al. |
| 5,269,306 A | 12/1993 | Warnking et al. |
| 5,273,028 A | 12/1993 | McLeod et al. |
| 5,284,143 A | 2/1994 | Rattner |
| 5,285,788 A | 2/1994 | Arenson et al. |
| 5,295,931 A | 3/1994 | Dreibelbis et al. |
| 5,301,683 A | 4/1994 | Durkan |
| 5,307,284 A | 4/1994 | Brunfeldt et al. |
| 5,309,898 A | 5/1994 | Kaufman et al. |
| 5,310,408 A | 5/1994 | Schryver et al. |
| 5,314,401 A | 5/1994 | Tepper |
| 5,316,000 A | 5/1994 | Chapelon et al. |
| 5,318,561 A | 6/1994 | McLeod et al. |
| 5,318,779 A | 6/1994 | Hakamatsuka et al. |
| 5,322,067 A | 6/1994 | Prater et al. |
| 5,323,769 A | 6/1994 | Bommannan et al. |
| 5,327,890 A | 7/1994 | Matura et al. |
| 5,330,481 A | 7/1994 | Hood et al. |
| 5,330,489 A | 7/1994 | Green et al. |
| 5,334,214 A | 8/1994 | Putnam |
| 5,339,804 A | 8/1994 | Kemp |
| 5,340,510 A | 8/1994 | Bowen |
| 5,351,389 A | 10/1994 | Erickson et al. |
| 5,363,850 A | 11/1994 | Soni et al. |
| 5,366,465 A | 11/1994 | Mirza |
| 5,367,500 A | 11/1994 | Ng |
| 5,376,065 A | 12/1994 | McLeod et al. |
| 5,380,269 A | 1/1995 | Urso |

| | | |
|---|---|---|
| 5,386,830 A | 2/1995 | Powers et al. |
| 5,393,296 A | 2/1995 | Rattner |
| 5,394,878 A | 3/1995 | Frazin et al. |
| 5,398,290 A | 3/1995 | Brethour |
| 5,400,795 A | 3/1995 | Murphy et al. |
| 5,405,389 A | 4/1995 | Conta et al. |
| 5,409,446 A | 4/1995 | Rattner |
| RE34,959 E | 5/1995 | Potts |
| 5,413,550 A | 5/1995 | Castel |
| 5,415,167 A | 5/1995 | Wilk |
| 5,417,215 A | 5/1995 | Evans et al. |
| 5,424,550 A | 6/1995 | Kawano et al. |
| 5,431,612 A | 7/1995 | Holden |
| 5,434,827 A | 7/1995 | Bolorforosh |
| 5,441,051 A | 8/1995 | Hileman et al. |
| 5,441,058 A | 8/1995 | Fareed |
| 5,448,994 A | 9/1995 | Iinuma |
| 5,460,595 A | 10/1995 | Hall et al. |
| 5,466,215 A | 11/1995 | Lair et al. |
| 5,468,220 A | 11/1995 | Sucher |
| 5,476,438 A | 12/1995 | Edrich et al. |
| 5,478,306 A | 12/1995 | Stoner |
| 5,492,525 A | 2/1996 | Gibney |
| 5,495,846 A | 3/1996 | Uehara et al. |
| 5,496,256 A | 3/1996 | Bock et al. |
| 5,501,657 A | 3/1996 | Feero |
| 5,507,800 A | 4/1996 | Strickland |
| 5,507,830 A | 4/1996 | DeMane et al. |
| 5,509,933 A | 4/1996 | Davidson et al. |
| 5,520,612 A | 5/1996 | Winder et al. |
| 5,524,624 A | 6/1996 | Tepper et al. |
| 5,526,815 A | 6/1996 | Granz et al. |
| 5,541,489 A | 7/1996 | Dunstan |
| 5,547,459 A | 8/1996 | Kaufman et al. |
| 5,556,372 A | 9/1996 | Talish et al. |
| 5,578,060 A | 11/1996 | Pohl et al. |
| 5,615,466 A | 4/1997 | Safari et al. |
| 5,626,554 A | 5/1997 | Ryaby et al. |
| 5,626,630 A | 5/1997 | Markowitz et al. |
| 5,630,837 A | 5/1997 | Crowley |
| 5,648,941 A | 7/1997 | King |
| 5,656,016 A | 8/1997 | Ogden |
| 5,680,863 A | 10/1997 | Hossack et al. |
| 5,690,608 A | 11/1997 | Watanabe et al. |
| 5,691,960 A | 11/1997 | Gentilman et al. |
| 5,699,803 A | 12/1997 | Carodiskey |
| 5,702,353 A | 12/1997 | Guzzini et al. |
| 5,702,389 A | 12/1997 | Taylor et al. |
| 5,706,818 A | 1/1998 | Gondo |
| 5,708,236 A | 1/1998 | Shaanan et al. |
| 5,721,400 A | 2/1998 | Haraldsson et al. |
| 5,725,482 A | 3/1998 | Bishop |
| 5,728,095 A | 3/1998 | Taylor et al. |
| 5,730,705 A | 3/1998 | Talish et al. |
| 5,738,625 A | 4/1998 | Gluck |
| 5,741,317 A | 4/1998 | Ostrow |
| 5,743,862 A | 4/1998 | Izumi |
| 5,755,746 A | 5/1998 | Lifshey et al. |
| 5,762,616 A | 6/1998 | Talish |
| 5,779,600 A | 7/1998 | Pape |
| 5,785,656 A | 7/1998 | Chiabrera et al. |
| 5,818,149 A | 10/1998 | Safari et al. |
| 5,829,437 A | 11/1998 | Bridges |
| 5,868,649 A | 2/1999 | Erickson et al. |
| 5,871,446 A | 2/1999 | Wilk |
| 5,886,302 A | 3/1999 | Germanton et al. |
| 5,891,143 A | 4/1999 | Taylor et al. |
| 5,899,425 A | 5/1999 | Corey Jr. et al. |
| 5,904,659 A | 5/1999 | Duarte et al. |
| 5,957,814 A | 9/1999 | Eschenbach |
| 5,962,790 A | 10/1999 | Lynnworth et al. |
| 5,971,984 A | 10/1999 | Taylor et al. |
| 5,997,490 A | 12/1999 | McLeod et al. |
| 6,019,710 A | 2/2000 | Dalebout et al. |
| 6,022,349 A | 2/2000 | McLeod et al. |
| 6,030,386 A | 2/2000 | Taylor et al. |
| 6,068,596 A | 5/2000 | Weth et al. |
| 6,080,088 A | 6/2000 | Petersen et al. |
| 6,086,078 A | 7/2000 | Ferez |
| 6,093,135 A | 7/2000 | Huang |
| 6,165,144 A | 12/2000 | Talish et al. |
| 6,179,797 B1 | 1/2001 | Brotz |
| 6,206,843 B1 | 3/2001 | Iger et al. |
| 6,213,958 B1 | 4/2001 | Winder |
| 6,261,221 B1 | 7/2001 | Tepper et al. |
| 6,261,249 B1 | 7/2001 | Talish et al. |
| 6,273,864 B1 | 8/2001 | Duarte |
| 6,355,006 B1 * | 3/2002 | Ryaby et al. .................. 601/2 |
| 6,360,027 B1 | 3/2002 | Hossack et al. |
| 6,394,955 B1 * | 5/2002 | Perlitz ........................ 600/439 |

FOREIGN PATENT DOCUMENTS

| | | |
|---|---|---|
| DE | 29811185 U1 | 10/1998 |
| EP | 0 181 506 A2 | 5/1986 |
| EP | 331 348 A1 | 9/1989 |
| EP | 0 536 875 A1 | 4/1993 |
| EP | 0 679 371 A1 | 11/1995 |
| EP | 0 695 559 | 2/1996 |
| EP | 0 965 839 A1 | 12/1999 |
| GB | 2156983 A | 10/1985 |
| GB | 2277448 A | 11/1994 |
| GB | 2 303 552 A | 2/1997 |
| JP | 621987-47359 | 3/1987 |
| JP | HEI 4-82567 | 3/1992 |
| JP | 41992-82568 | 3/1992 |
| JP | 41992-82569 | 3/1992 |
| JP | 51993-269159 | 10/1993 |
| WO | WO 85/03449 | 8/1985 |
| WO | WO 88/00845 | 2/1988 |
| WO | WO 88/02250 | 4/1988 |
| WO | WO 90/06720 | 6/1990 |
| WO | WO 94/13411 | 6/1994 |
| WO | WO 95/03744 | 2/1995 |
| WO | WO 95/33416 | 12/1995 |
| WO | WO 96/25112 | 8/1996 |
| WO | WO 96/25888 | 8/1996 |
| WO | WO 97/33649 | 9/1997 |
| WO | WO 98/10729 | 3/1998 |
| WO | WO 98/34578 | 8/1998 |
| WO | WO 98/47570 | 10/1998 |
| WO | WO 99/18876 | 4/1999 |
| WO | WO 99/22652 | 5/1999 |
| WO | WO 99/48621 | 9/1999 |
| WO | WO 99/56829 | 11/1999 |
| WO | WO 99/58080 | 11/1999 |
| WO | WO 00/03663 | 1/2000 |
| WO | WO 00/28925 | 5/2000 |
| WO | WO 00/71207 | 11/2000 |
| WO | WO 00/76406 | 12/2000 |

OTHER PUBLICATIONS

McLeod, et al., "Improved Postural Stability Following Short Term Exposure to Low Level Whole Body Vibration," 44$^{th}$ Annual Meeting, Orthopaedic Reasearch Society, Mar. 16–19, 1998, New Orleans, Louisiana, p. 89–15.

Phoenix (Business Wire), Jul. 8, 1997 via CompanyLink—OrthoLogic Corp.

Pilgrim, et al., "An Extension of the Composite Nomenclature Scheme," Med. Res. Bull., vol. 22, pp. 877–894 (1987).

"Reflex Sympathetic Dystrophy, Does RSD Exist?" www.arbon.com (Jun. 4, 1997).

"Reflex Sympathetic Dystrophy: The Pain That Doesn't Stop," tcc.cc.nc.us (Jun. 4, 1997).

RSDnet.org "Reflex Sympathetic Dystrophy," www.rsdnet.org (Jun. 4, 1997).

Tavakoli and Evans, "The Effect of Bone Structure on Ultrasonic Attenuation and Velocity," *Ultrasonics*, vol. 30, No. 6 (1992).

Caplan, et al., *Clinical Orthopaedics and Related Research*, No. 342:254–269 (1997).

Moran, et al., *The Journal of Bone and Joint Surgery*, 74–B:659–667 (1992).

Abstract, (Proceedings of the 11$^{th}$ Int'l. Conference on Medical and Biological Engineering) "Ultrasonic Stimulation of Fracture Healing", 1976.

Abstract, (Proceedings of the lil Congress on Biomedical Engineering) "Ultrasonic Action on Callus Formation in Bones", 1975.

Abstract, (Proceedings of the IV Brazilain Congress on Biomedical Engineering) "Ultrasound in the Treatment of Fractures", 1977.

ASTM Designation: D790M–93 Metric, "Standard Test Methods for flexural Properties of Unreinforced and Reinforced Plastics and Electrical Insulating Materials [Metric]", pp. 176–184, (Dec. 1993).

ASTM Designation: C1161–90, "Standard Test Method for Flexural Strength of Advanced Ceramics at Ambient Temperature," pp. 324–330.(Feb. 1991).

7Brochure: "The Science Behind the Technology," distributed by Smith & Nephew for EXOGEN. (no date).

Aral et al., "The Effect of Ultrasound Stimulation on Disuse Osteoporosis", Brags 17, 1993.

Berridge, M.J., "Inositol Trisphosphate and Calcium Signaling", *Nature* (1993), 361:315–325.

Duarte, L.R., "The Stimulation of Bone Growth by Ultrasound", *Arch. Orthrop. Trauma Surg* (1983), 101: 153–159.

Dyson, M., "Therapeutic Applications of Ultrasound", *Biological Effects of Ultrasound* (1985), Nyborg, W.L. and Ziskin, M.C., eds; Churchill Livingstone Inc., New York, Chapter 11.

Goodship, A.E. et al., "The Influence of Induced Micromovement Upon the Healing of Experimental Tibial Fractures", *J. Bone and Joint Surg.* (1985), 67–B(4):650–655.

Heckman, J.D. et al., "Acceleration of Tibial Fracture Healing by Non–Invasive Low–Intensity Pulsed Utrasound", *J. Bone and Joint Surg.* (1994), 76–A(1): 26–34.

Howkins, S.D., "Diffusion Rates and the Effect of Ultrasound", *Ultrasonics* (1969), 129–130.

Kristiansen, T.K. et al., "Accerlated Healing of Distal Radial Fractures with the Use of Specific, Low–Intensity Ultrasound", *J. Bone and Joint Surg.* (1997), 79–A(7) 961–973.

Maurice Hilario, "Low–Intensity Ultrasound Radiation in the Tissue Repair of Trophic Leg Ulcers", 1983, University of Sao Paulo, pp. 1–125.

Ter Haar, G., et al., "Basic Physics of Therapeutic Ultrasound", *Physiotherapy* (1987), 73(3): 110–113.

Wallace, A.L.; Draper E.R.C.; Strachan, R.K.; McCarthy, I.D.; Hughes, S.P.F., "The Vascular Response to Fracture Micromovement", *Clinical Orthopeedics and Related Research* (1994), 301: 281–290.

Wang, S.J. et al., "Low–Intensity Ultrasound Treatment Increases Strength in a Rat Femoral Fracture Model", *J. Ortho Research* (1994), 12: 40–47.

Webster, D.F. et al., "The Role of Ultrasound–Induced Cavitation in the 'In Vitro' Stimulation of Collagen Synthesis in Human Fibroblasts", *Ultrasonics* (1980), 33–37.

Yang, K.H. et al., "Exposure to Low–Intensity Ultrasound Treatment Increases Aggrecan Gene Expression in a Rat Femur Fracture Model", *J. Ortho Research* (1996), 14:802–809.

Treatment of Osteochondral Defects in Rabbits with SAF-HS–Parts I and II, EX1095–01R, EX1096–01R.

Treatment of Osteochondral Defects in Rabbits with SAF-HS–Part III, EX1097–01R (Aug. 26, 1997).

Cook, Stephen and L. Patron, "Treatment of Osteochondral Defects in Rabbits with SAFHS–A Mosaicplasty Model"–Final Report, EX1098–04R (Aug. 12, 1999).

Acoustic Emission–An Update, by Arthur E. Lord, Jr., 1981, Physical Acoustics, vol. XV, pp. 295–360.

Acoustic Emission and Diagnosis of Osteoporosis, by S. Hanagud, G. T. Hannon and R. Clinton, 1974, Ultrasonic Symposium Proceedings (IEEE), pp. 77–81.

Acoustic Emission in Bone Substance, by S. Hangud, R.G. Clinton and J.P. Lopez, 1973, Biomechanics Symposium Proceedings (ASME), pp. 79–81.

Acoustic Emission Inspection, by Adrian A. Pollock, 1992, ASM Handbook, vol. 17 Nondestructive Evaluation and Quality Control, pp. 278–293.

Acoustic Emission Techniques in the Development of a Diagnostic Tool for Osteoporosis, by S. Hanagud and R. G. Clinton, 1975, Ultrasonic Symposium Proceedings (IEEE), pp. 41–45.

Application of an intelligent signal processing system to acoustic emission analysis, by Igo Grabec and Wolfgang Sachse, Mar. 1989, Acoustic Society of America, pp. 787–791.

Application of correlation techniques for localization of acoustic emission sources, by I. Grabec, 1978, IPC Business Press Ltd., pp. 111–115.

Cornejo, et al., "Large–Area Flexible–Array Piezoelectric Ceramic/Polymer composite Transducer for Bone Healing Acceleration," presented at ISAFXI, Montreux, Switzerland (1998).

Clough, R. and J. Simmons, "Theory of Acoustic Emission," Metallurgy Division, national Bureau of Standards. (no date).

Fritton, et al., "Whole–Body Vibration in the Skeleton: Development of a Resonance–Based Testing Device," *Annals of Biomedical Engineering*, vol. 25, pp. 831–839 (1997).

J. Kenwright, et al., "Controlled Mechanical Stimulation in the Treatment of Fibial Fractures," Orthopedics, Clinical Orthopedics and Related Research (1989) 241:36–47.

Jankovich, "The Effects of Mechanical Vibration on Bone Development in the Rat," *J. Biomechanics*, 1972, vol. 5, pp. 241–250.

Ko, "Preform Fiber Architecture for Ceramic–Matrix Composites," Ceramic Bulletin, vol. 68, No. 2, pp. 401–414(1989).

Newnham, et al., Connectivity and Piezoelectric–Pyroelectric Composites, Med. Res. Bull., vol. 13, pp. 525–536 (1978).

Pauer, "Flexible Piezoelectric Material," pp. 1–5, (no date).

Powell, et al., "A Performance Appraisal of Flexible Array Structures Using a Facet Ensemble Scattering Technique," 1991 *Ultrasonic Symposium*, pp. 753–766.

Powell, et al., Flexible Ultrasonic Transducer Arrays for Nondestructive Evaluation Applications –Part I: The Theoretical Modeling Approach, "*IEEE Transactions on Ultrasonics, Ferroelectrics, and Frequency Control,*" vol. 43, No. 3, May 1996, pp. 385–392.

Powell, et al., "Flexible Ultrasonic Transducer Arrays for Nondestructive Evaluation Applications –Part II: Performance Assessment of different Array Configurations," *IEEE Transactions on Ultrasonics, Ferroelectrics, and Frequency Control*, vol. 43, No. 3, May 1996, pp. 393–402.

Sarvazyan, "Some General Problems of Biological Action of Ultrasound," IEEE Transactions on Sonics and Ultrasonics, vol. 30, No. 1, Jan. 1983.

Ultrasound as a Tool for Investigating Bone: Fundamental Principles and Perspectives for Use in Osteoporosis, by J. G. Bloch, 1993, Expanson Scientifique Francaise.

"Development of Flexible Pieoelectric Transducers and Matching Layers for EXOGEN Incorporated," Final Report, Covering Period Apr. 1, 1997 to Feb. 28, 1998, Rutgers University.

Grewe, Martha G., "Acoustic Matching And Backing Layer for Medical Ultrasonic Transducers," A Thesis in Solid State Science, The Pennsylvania State University; (May 1989), The Center for Ceramics Research, Rutgers.

Gururaja, T., "Piezoelectric Composite Materials for Ultrasonic Transducer Applications," A Thesis in Solid State Science, The Pennsylvania State University, May 1984.

Gururaja, "Piezoelectrics for Medical Ultrasonic Imaging," *Am. Ceram. Soc. Bull.*, vol. 73, No. 5, pp. 50–55 (May 1994).

Hall, et al., "The design and evaluation of ultrasonic arrays using 1–3 connectivity composites," *SPIE*, pp. 216–227, vol. 1733 (1992).

Pilla, et al., "Non–Invasive Low–Intensity Pulsed Ultrasound Accelerates Bone Healing in the Rabbit," *Journal of Orthopaedic Trauma*, vol. 4, No. 3, pp. 246–253 (1990).

Safari, "Development of piezoelectric composites for transducers," *J. Phys.France*, 4:1129–1149 (1994).

Selfridge, "Approximate Material Properties in Isotropic Materials," *IEEE Transactions on Sonics and Ultrasonics*, May 9, 1985.

Souquet, et al., "Design of Low–Loss Wide–Band Ultrasonic Transducers for Noninvasive Medical Application," *IEEE Transactions on Solid and Ultrasonics*, pp. 75–81, vol. SU–26, No. 2, Mar. 1979.

Waller, et al., "Poling of Lead Zirconate Titanate Ceramics and Flexible Piezoelectric Composites by the Corona Discharge Techique," *J. Am. Ceram. Soc.*, 72(2):322–24 (1989).

Winder, Alan, "Synthetic Structural Imaging and Volume Estimation of Biological Tissue Organs," Acoustic Sciences Associates, Dec. 1995.

Winder, Alan, "Acoustic Emission Monitoring for the Detection, Localization and Classification of Metabolic Bone Disease," Acoustic Sciences Associates, Dec. 1995.

Pethica, B.A., et al., Abstract, Biological Repair and Growth Society, Jun. 1998.

Goodship, et al., "Low magnitude high frequency mechanical stimulation of endochondral bone repair" $43^{rd}$ Annual Meeting Orthopeadic Research Society, vol. 22, Sec. 1, Feb. 9–13 (1997).

Y. Qin, et al., "Correlation of In Vivo Bone Adaptation and Mechanical Parameters Using Low Magnitude, High Frequency Loading," $41^{st}$ Annual Meeting Orthopaedic Research Soc., vol. 20 –Sec. 1, Feb. 13–16 (1955).

Grewe, et al., "Acoustic Properties of Particle Polymer Composite for Ultrasonic Transducer Backing Applications," *IEEE*, (1990).

Wu and Cubberly, "Measurement of Velocity and Attenuation of Shear Waves in Bovine Compact Bone Using Ultrasonic Spectroscopy," Med. & Biol., vol. 23, No. 1,129–134, 1997.

Pilla, et al., "Non–Invasive Low–Intensity Pulsed Ultrasound Accelerates Bone Healing in the Rabbit," *Journal of Orthopaedic Trauma*, vol. 4, No. 3, pp. 246–253 (1990).

Bascom, "Other Continous Fibers," 118/Constitutent Material Form.

Bascom, "Other Discontinous Forms," 120/Constituent Material Forms.

Niemczewaki, B., "A Comparison of Ultrasonic Cavitation Intensity in Liquids," *Ultrasonics*, May 1980, pp. 107–110.

* cited by examiner

TRANSDUCER MOUNTING ASSEMBLY

This application claims benefit of the filing date of U.S. Provisional Application Ser. No. 60/242,994, filed Oct. 25, 2000, the entire contents of which are incorporated herein by reference.

BACKGROUND OF THE INVENTION

1. Field of the Invention

The invention relates to an apparatus for adjustably mounting an ultrasonic transducer to an orthopedic appliance, wherein the transducer can be adjustably positioned in a manner appropriate for ultrasonic therapy.

2. Description of Related Art

The use of ultrasound therapy for the acceleration of healing of bone injuries is known in the art. Similarly, the acceleration of healing of soft tissue injuries, particularly musculoskeletal tissues, by the application of ultrasound has also been described. Ultrasonic therapy generally involves placing an ultrasonic transducer, usually associated with a conductive gel or bladder, against or near the skin in the vicinity of the injury, and driving the transducer with a signal generator, so that the transducer delivers ultrasonic waves within a particular range of therapeutically effective frequencies for a period of time and for a sufficient number of applications to achieve effective results in accelerating healing. See, e.g., U.S. Pat. Nos. 6,273,864; 6,190,336; 5,762,616; and 5,520,612, the entire contents of each of which are incorporated herein by reference.

Ultrasonic therapy can be particularly useful in treating injuries, such as severe fractures or soft tissue injuries and the like, that require either support or immobilization of a joint or immobilization of bones relative to each other at a fracture site, using some form of orthopedic appliance.

These types of injuries are often treated by the application of a brace, fixator, cage, or other orthopedic appliance to the site of the injury to immobilize the affected area or to limit the range of motion during healing, e.g., occurring after orthopedic surgery. Placement of ultrasonic transducer heads in positions most appropriate for accelerating healing may be impeded by elements of the orthopedic appliance when existing attachment techniques, such as straps or bandages, are used.

In addition, ultrasonic treatment is often of great benefit in speeding healing by patients that have been discharged from the hospital and are convalescing. The frequency of treatments and the difficulty patients often have with locomotion make home treatment desirable. As a result, ultrasonic treatment is often self-administered by the patient following physician instruction in use of the device. However, existing attachment techniques rely on patient compliance in accurately positioning the transducer. Because patients can be inconsistent in positioning the transducer, applying conductive gel to the proper location, etc., there exists a need in the art for a mechanism for adjustably mounting an ultrasonic transducer to an orthopedic appliance so that the transducer can consistently and reliably be brought into contact with the desired treatment site without interfering with or interference from the appliance.

SUMMARY OF THE INVENTION

The apparatus of the invention allows an ultrasonic transducer to be secured to an orthopedic appliance in an adjustable fashion, so that the transducer can be consistently and reliably moved into the proper position for treatment, without interference from or interfering with the elements of the orthopedic appliance, and then can be moved out of the way or removed during periods between treatments.

In one embodiment, the invention relates to an apparatus for adjustably securing an ultrasonic transducer to an orthopedic appliance, having:

(a) an optional adjustable clamp adapted to adjustably secure the apparatus to an element of an orthopedic appliance;

(b) a transducer holder adapted to secure the transducer to the apparatus;

(c) an adjustable connector adapted to adjustably connect the optional adjustable clamp to the transducer holder.

The configuration of the optional adjustable clamp may take various forms in order to allow the apparatus to be secured to a variety of orthopedic appliances.

As described in more detail below, the apparatus may take the form of one of several alternative embodiments, each of which allow attachment to one or more elements of existing orthopedic appliances, and allow the ultrasonic transducer to be adjustably and reliably positioned relative to the patient.

DETAILED DESCRIPTION OF SPECIFIC EMBODIMENTS

Figure 1:
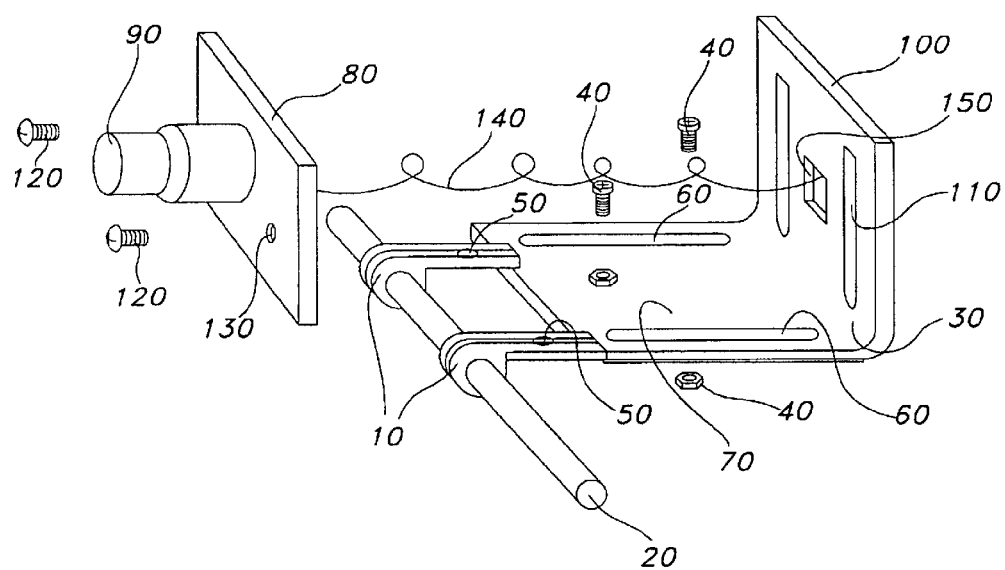
FIG. 1 is an exploded perspective view of the apparatus of one embodiment of the invention secured to an element of an orthopedic appliance.

The apparatus of the invention is intended to be attachable to a variety of orthopedic appliances, ranging from external fixators, such as Ilizarov rings, unilateral fixators, or spatial frames (such as those disclosed in U.S. Pat. Nos. 6,030,386; 5,971,984; 5,891,143; 5,728,095; and 5,702,389, the entire contents of each of which are incorporated herein by reference), to orthopedic braces and the like. As a result, the particular configuration of the adjustable clamp may be substantially variable. It may be adjustable in the sense that it can be attached to the orthopedic appliance in a variety of locations or positions, or in the sense that the clamp allows movement relative to the element of the orthopedic element to which it is attached, or in the sense that the attachment point of the clamp to the adjustable connector can be varied, or some combination thereof. The adjustable clamp may, in fact, be available or sold with the orthopedic appliance itself, and in that sense is optional.

As an example, when the apparatus of the invention is to be affixed to the ring of an external ring fixator, a fixator clamp, also known as a "Rancho cube," may be used to adjustably clamp the apparatus to the ring. Another example of an adjustable clamping mechanism includes one or more hinges, which may be used to secure the device to various points on rods or other rigid elements of the orthopedic appliance, such as the rods of a ring fixator. These hinges may allow movement of the adjustable connector relative to the attachment point as the hinges rotate. Other examples of suitable clamps include bolts, screw clamps, spring clamps, standard laboratory clamps, and the like, whose position on the orthopedic appliance may be varied.

The transducer holder is adapted to attach the transducer to the device. It may be removable from the transducer, such as a cap into which the transducer may be inserted, or it may be permanently affixed to the transducer. The transducer holder may be a threaded opening in or threaded stud mounted on a nonoperative surface of the transducer, with which a correspondingly threaded stud or threaded opening on or attached to the adjustable connector may be inserted. Other arrangements include non-threaded openings/studs secured by set screws and the like, ball-and-socket joints affixed to a nonoperative transducer surface, and the like.

The adjustable connector provides, in effect, an adjustable link between the transducer holder and the adjustable clamp. The connector may be adjustable in the sense that the attachment point of the adjustable clamp can be varied, or in the sense that the attachment point of the transducer holder may be varied, or in the sense that the connector itself contains moveable parts whose positioning can be adjusted, or in the sense that the connector allows the transducer and transducer holder to be removed when not in use, or any combination of these. In any event, the connector allows for the position of the transducer holder, and thus of the transducer, to be varied relative to the adjustable clamp.

One example of an adjustable connector is a plate, which may be substantially flat or which may be angled, having one or more slots for adjustable attachment of the adjustable clamp, the transducer holder, or both. Another example is an articulating arm, attached through an adjustable bracket, a threaded stud/opening arrangement, or a ball-and-socket joint, to the transducer holder at one end, and bolted or clamped to an element of the orthopedic appliance at the other end. This articulating arm may be made from a flexible articulated material having a plurality of joints, or may be made from a few rigid elements having swivel joints and lockable slide collars. Another example of an adjustable connector includes a shaft secured to the transducer holder on one end and having an optional handle at the other end, which is disposed in a barrel assembly which allows the shaft to move within the barrel, and which barrel assembly contains a pin which can be adjustably secured by the clamp.

The invention will be further described by reference to certain of its specific embodiments illustrated in the accompanying drawings. This description and the drawings are not intended to be limitative of the appended claims.

FIG. 1 shows an embodiment of the invention wherein optional adjustable clamp contains hinge 10, which is rotatably attached to an element of an orthopedic appliance 20. Hinge 10 is adjustable because it can rotate about the longitudinal axis of element 20, and may optionally also be moveable along its length. Hinge 10 can be adjustably secured to adjustable connector 30 by a fastener 40, illustrated as a threaded bolt and nut combination. The fastener 40 passes through hole 50 in hinge 10, and then passes through slot 60 in first leg 70 of the adjustable connector 30. This allows the location of the hinge 10 along the first leg 70 to be adjusted by sliding fastener 40 along slot 60 and tightening the fastener when the hinge 10 and adjustable connector 30 are in the appropriate relative position.

Transducer holder 80 comprises a plate affixed to transducer 90 and fastened to second leg 100 of adjustable connector 30 by a fastener 120, which passes through hole 130 in plate 80, and which also passes through slot 110 in second leg 100. The fastener illustrated is a bolt which is secured by a correspondingly threaded nut (not shown) after passing through slot 110. It will be recognized that any fastener that can be tightened, loosened, and retightened securely will function to provide the desired adjustability in securing the transducer holder to the adjustable connector, and in securing the clamp to the adjustable connector. As illustrated, adjustable connector 30 contains an opening 150 to accommodate a cable 140 powering the transducer 90.

As illustrated, adjustable connector 30 is a rectangular, angled plate having two legs approximately perpendicular (oriented at about 90°) relative to each other. It will be recognized that other shapes and orientations may be used and still fall within the spirit and scope of the invention. For example plates that are circular or oval or have another geometrical shape, or that are angled at acute or obtuse angles, or that are substantially flat, could also be used in the invention.

Figure 2:
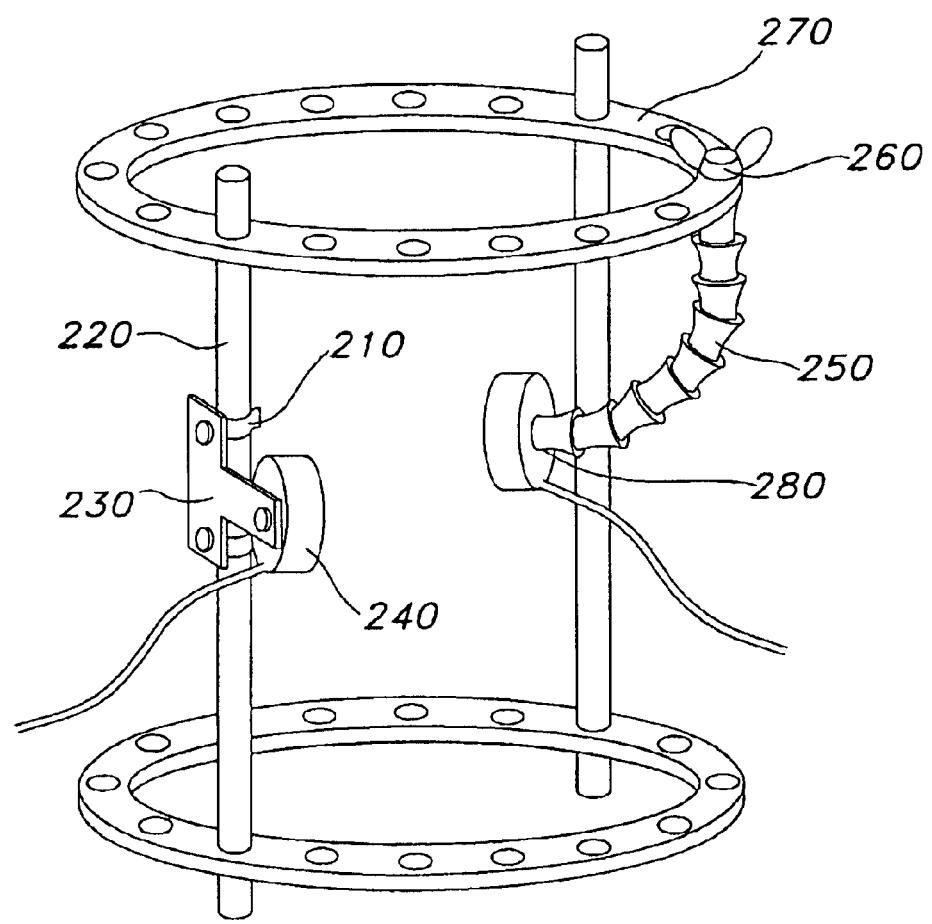
FIG. 2 is a perspective view of two embodiments of the invention secured to an external ring fixator.

An example of an embodiment of the invention using a flat plate 230 as the adjustable connector between transducer holder 240 and clamp 210 is shown in FIG. 2. Clamp 210, as illustrated, secures the apparatus of the invention to an element of an external ring fixator.

Figure 3:
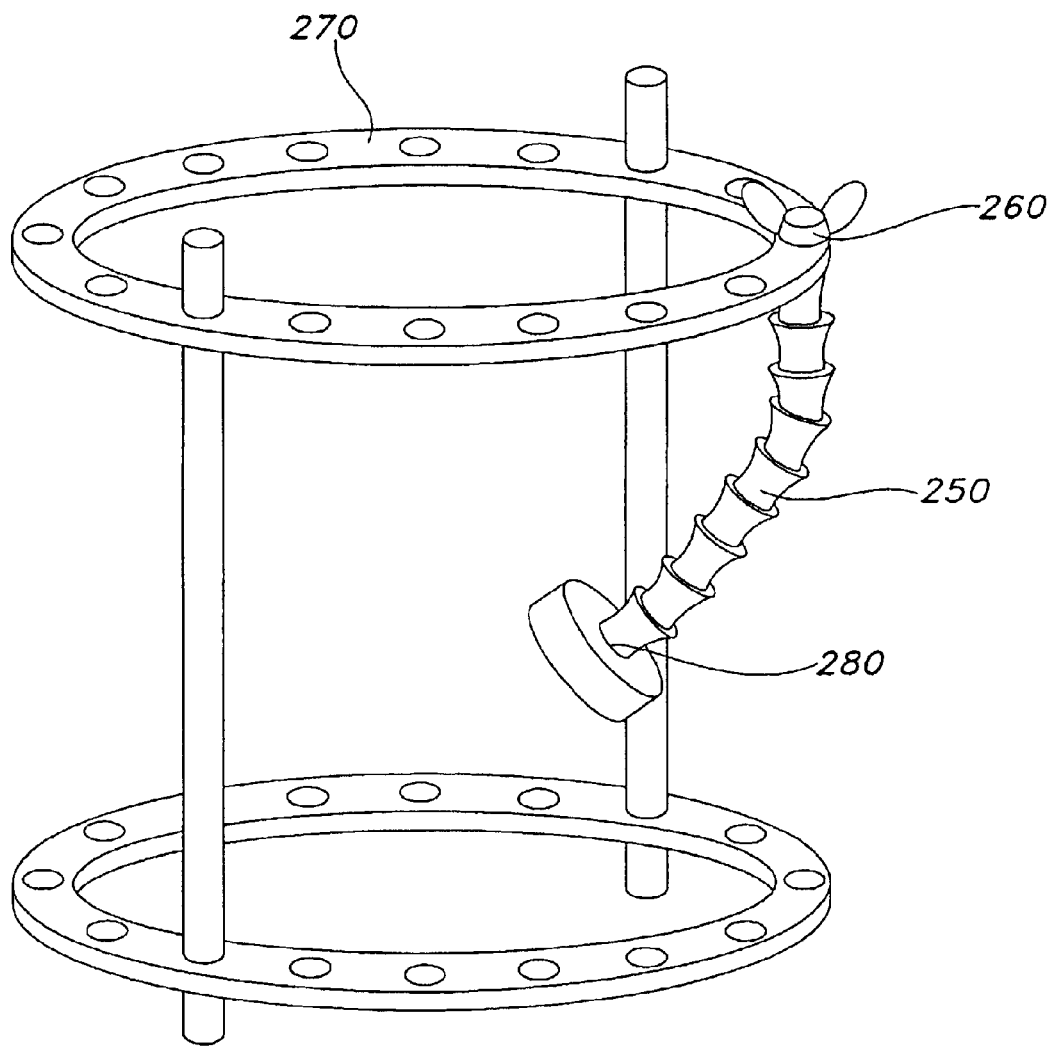
FIG. 3 is an enlarged perspective view of the apparatus of one of the embodiments of the invention shown in FIG. 2, secured to an external ring fixator.

Also illustrated in FIG. 2 and FIG. 3, and shown secured to a ring 270 of an external ring fixator, is another embodiment of the apparatus of the invention wherein the adjustable connector comprises a flexible arm 250, which connects clamp 260 to transducer holder 280. As illustrated, flexible arm 250 is a multijointed flexible articulating arm. Suitable materials for such a flexible articulating arm include MEDI-FLEX® (Flexbar Machine Corp.), Lockline flexible arm materials, or other flexible arm materials or "goosenecks." It is generally desirable that these articulating arms be lockable, so that once oriented, their reorientation requires application of suitable force. This allows for adjustability but also helps to prevent the arms from being inadvertently knocked out of position during treatment. It is also desirable that the articulating arm be such that additional articulating joints can be added to the arm or removed from the arm as needed, in order to adjust the length of the arm as necessary to treat a particular injury.

Figure 4:
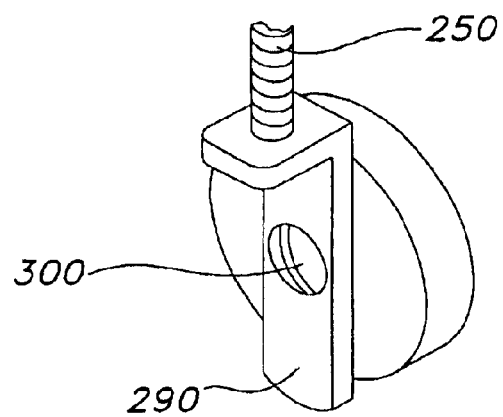
FIG. 4 is a perspective view of one embodiment of a transducer holder according to the invention.

Suitable transducer holders for use in connection with this embodiment of the invention include a ball-and-socket joint affixed to the non-operative surface of the transducer (or to a cap into which the transducer can be inserted), and capable of attachment to, and articulation with, the flexible arm. An alternative embodiment of transducer holder is shown in FIG. 4, which shows a bracket 290 attached to flexible arm 250 and also attached to a transducer or cap for holding a transducer by suitable fastener 300 (e.g., a bolt, screw, or rivet). Desirably, the transducer-holder is capable of holding an EXOGEN 3000 brand transducer or a similar transducer.

As illustrated in FIG. 2 and FIG. 3, a wingnut is used to clamp one end of the flexible arm to the ring of the fixator; it will be recognized that a hinged clamp, such as that shown in FIG. 1, could also be used to clamp the articulating arm to a vertical rod of the fixator ring, or to a unilateral fixator or an orthopedic brace within the scope of the invention. Alternatively, a no-hole clamp, such as that shown in FIG.

5, which does not rely on the presence of holes in the ring, or spring clamps, standard laboratory clamps, screw clamps, or other clamp mechanisms could be used to secure the apparatus to the orthopedic appliance.

Figure 5:
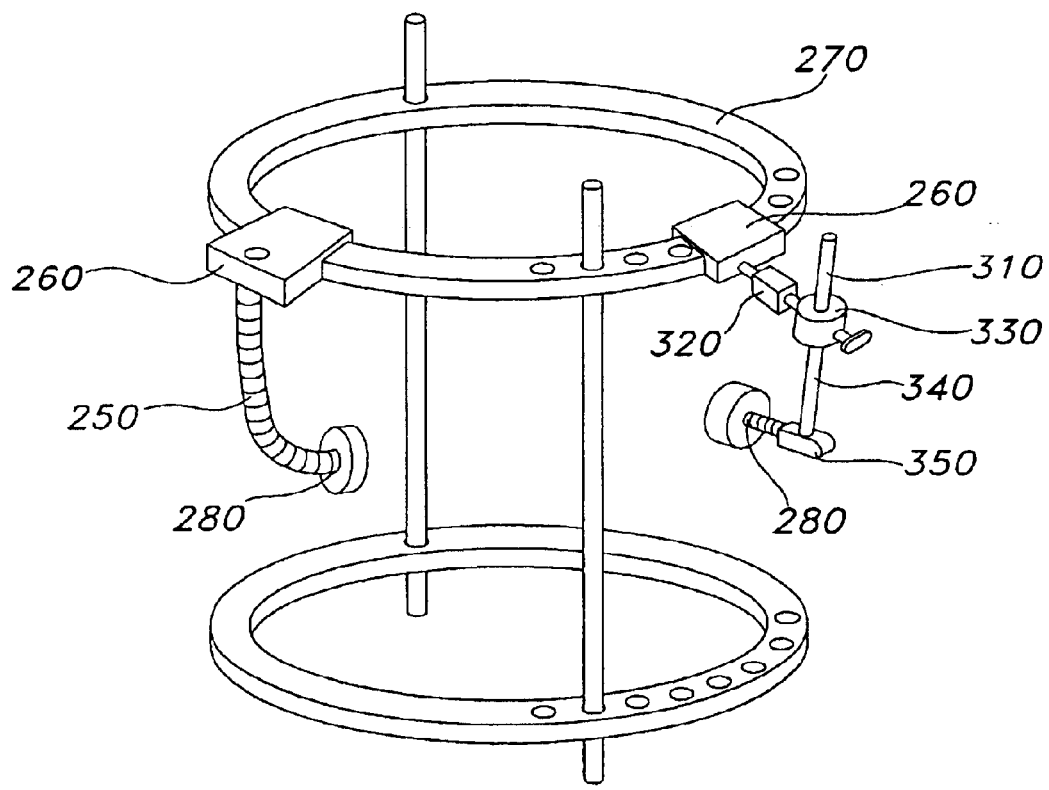
FIG. 5 is a perspective view showing two embodiments of the apparatus of the invention secured to an external ring fixator.

FIG. 5 also illustrates an alternative configuration for the apparatus of the invention, wherein a clamp 260 is used to secure the apparatus to a ring of an external fixator, which may be any of the clamp mechanisms described above for use with a flexible articulating arm. Instead of the multi-jointed flexible articulating arm described above, this configuration uses an articulating arm 310 having a first swivel joint 320 adapted to be secured by clamp 260 and attached to slide collar 330. Slide collar 330 can be adjustably positioned along rod 340, which is attached to second swivel joint 350, which is adapted to attach to transducer holder 280, which may be a threaded stud adapted to be inserted into a correspondingly threaded opening on the nonoperative surface of the transducer, or of a cap into which the transducer may be inserted.

Figure 6:
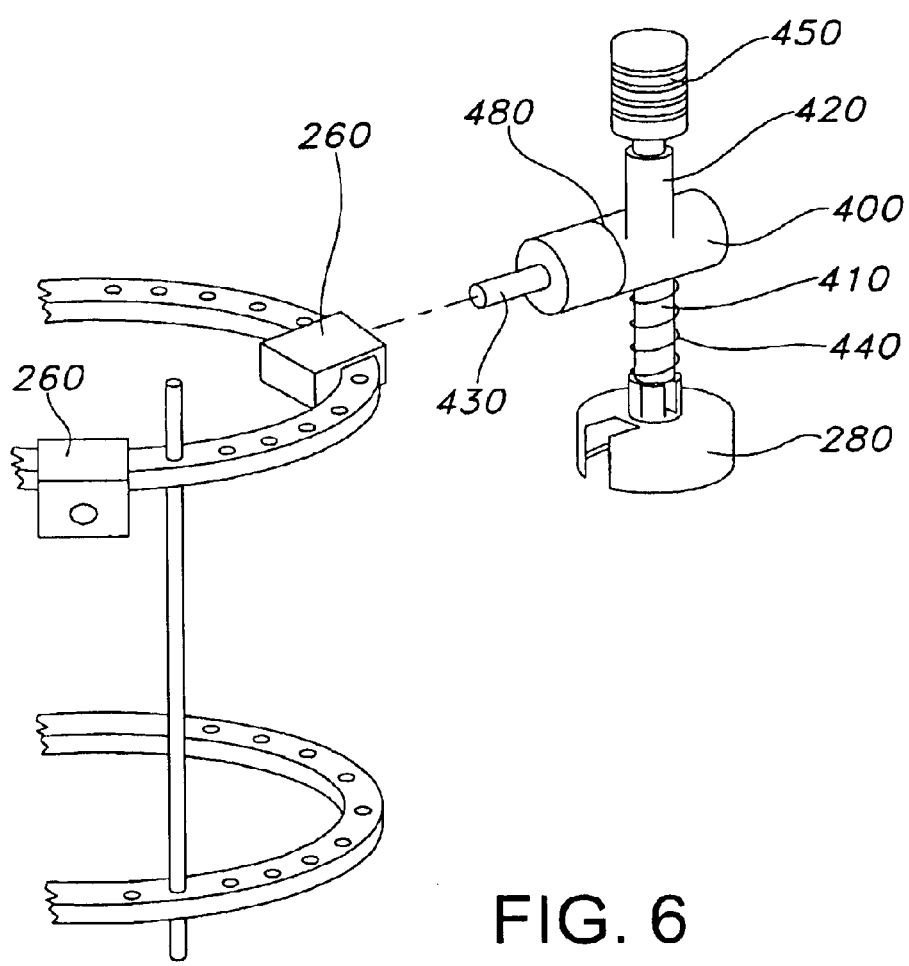
FIG. 6 is a perspective view of another embodiment of the apparatus of the invention.
Figure 7:
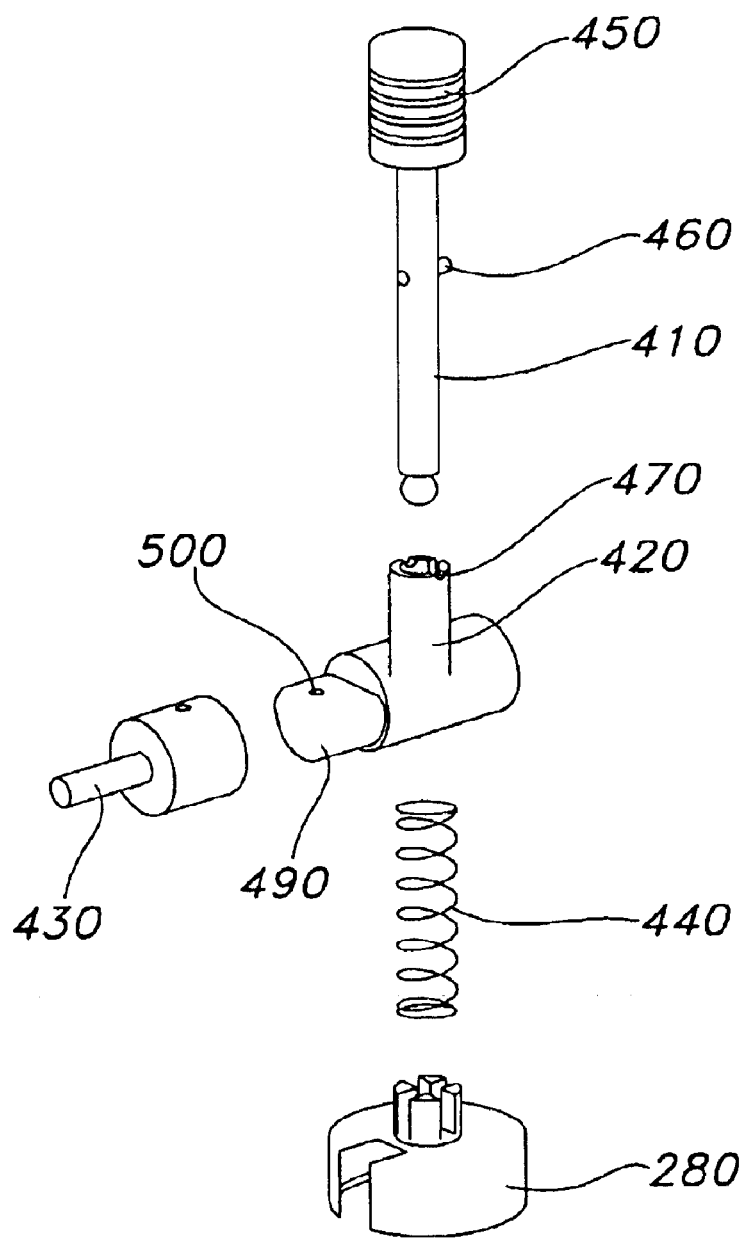
FIG. 7 is an exploded perspective view of the embodiment of the invention illustrated in FIG. 6.

FIG. 6 is a perspective view of another embodiment of the apparatus of the invention, and FIG. 7 provides an exploded perspective view of this embodiment. Transducer holder 280 is a cap adapted to receive the transducer and hold it in place, either by press fitting or by means of a set screw, and to attach to adjustable connector 400 by shaft 410. Shaft 410 moves in barrel 420, so that the position of transducer holder 280 relative to adjustable connector 400 can be varied. Adjustable connector 400 also contains pin 430, illustrated as extending orthogonally to barrel 420, which is adapted to be received by a clamp (not shown) and adjustably secured thereby. Desirably, pin 430 is sized and configured so as to be securable by a standard fixator or other clamp, such as a rancho cube, where it can be secured by a set screw at the desired level of the cube after being rotatably positioned. The location of the cube on the orthopedic appliance can also be varied or adjusted, providing additional flexibility in use. Alternatively, the pin can be threaded and screwed onto a ring of an external ring fixator using a wingnut or other fastener. Most desirably, the pin may be threaded, but sized to fit a rancho cube, enabling the apparatus to be secured in a variety of ways to a variety of elements of the orthopedic appliance.

Figure 7A:
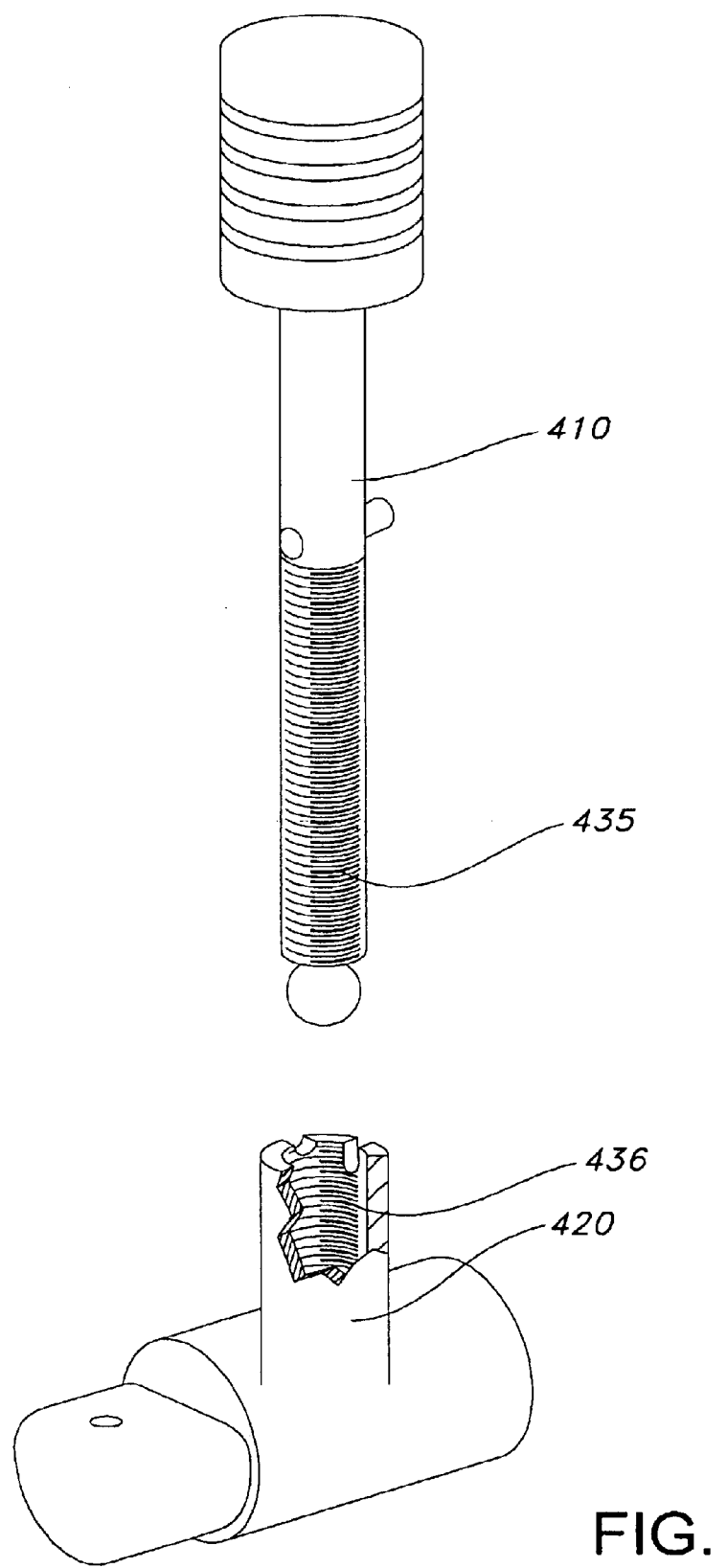
FIG. 7A is an exploded view of the shaft and barrel of FIG. 7.

In addition, shaft 410 and barrel 420 may be correspondingly threaded as shown by respective threads 435, 436 in FIG. 7A, so that the position of shaft 410 in barrel 420 may be adjusted by rotating shaft 410 relative to barrel 420. Alternatively, as illustrated, adjustable connector 400 may contain a biasing element 440 (illustrated as a coil spring disposed around the shaft 410) to urge the transducer holder away from the barrel and against the body of the patient. Optional handle 450 is provided in the illustrated embodiment for ease of adjustment of the apparatus. If the shaft and barrel are threaded, turning the handle will move the threaded shaft relative to the barrel, and allow adjustment of the position of the transducer holder relative to the patient. If a biasing element is present, the transducer can be moved by pulling the shaft against the biasing force exerted by the biasing element and locking the shaft in this retracted position (engaging optional locking pin 460 with optional locking slot 470, shown in FIG. 7) or by releasing the shaft when the transducer is appropriately positioned relative to the patient, so that the biasing element forces the transducer against the patient during treatment.

As illustrated, adjustable connector is optionally jointed at joint 480 (FIG. 6) in order to allow pin 430 to remain positioned appropriately in the adjustable clamp, while the remainder of adjustable connector 400 is removed between treatments or for adjustment or repair. This joint is illustrated as a male D-element (a male element having a D-shaped cross section) on the barrel side of the adjustable connector, which corresponds to a female D-element (a female element having a D-shaped cross section) on the pin side of the adjustable connector. Retaining ball 500 holds the joint in place until the two sides of the adjustable connector are forced apart. It will be recognized that, if this removability feature is not desired or necessary, joint 480 can be eliminated from the apparatus, and that different joint configurations can be used, as long as they perform the function of removably attaching the transducer holder to the pin without allowing the joint to rotate, or the apparatus to rotate once it is secured in the clamp.

The invention also relates to a method of using the device described above. The device, or a portion thereof, can be attached to an orthopedic appliance, typically to a rigid element of the orthopedic appliance, via the clamp. The transducer can be attached to the transducer holder (if detachable) and the clamp, adjustable connector, and optionally the transducer holder adjusted to the appropriate orientation to deliver suitable ultrasound therapy. The adjustability of the device allows the transducer to be consistently and reliably positioned at the appropriate location without interference from or with the orthopedic appliance. Ultrasonic therapy can be delivered, and the device moved away from the treatment site and optionally detached (in some embodiments) from the appliance. Alternatively, the transducer can be removed from the device if desired

What is claimed is:

1. An apparatus for adjustably securing an ultrasonic transducer to an orthopedic appliance, comprising:

(a) an adjustable clamp adapted to adjustably secure the apparatus to an element of an orthopedic appliance;

(b) a transducer holder adapted to secure the transducer to the apparatus, wherein the transducer holder comprises a cap adapted to receive and retain the ultrasonic transducer; and (c) an adjustable connector adapted to adjustably connect the adjustable clamp to the transducer holder, wherein the adjustable connector comprises a shaft extending from a surface of the cap and a barrel adapted to receive the shaft, and further comprises a pin extending from the connector at an angle relative to the barrel, wherein the pin is adapted to be adjustably received by the adjustable clamp, and wherein the shaft and barrel are threaded with complementary threads.

2. The apparatus of claim 1, wherein the angle is around 90°.

3. The apparatus of claim 1, wherein the pin is threaded.

4. An apparatus for adjustably securing an ultrasonic transducer to an orthopedic appliance, comprising:

(a) an adjustable clamp adapted to adjustably secure the apparatus to an element of an orthopedic appliance;

(b) a transducer holder adapted to secure the transducer to the apparatus, wherein the transducer holder comprises a cap adapted to receive and retain the ultrasonic transducer; and (c) an adjustable connector adapted to adjustably connect the adjustable clamp to the transducer holder, wherein the adjustable connector comprises a shaft extending from a surface of the cap and adapted to cooperate with a barrel adapted to receive the shaft, and further comprises a pin extending from the connector at an angle of around 90° relative to the barrel, wherein the pin is adapted to be adjustably received by the adjustable clamp, and wherein the adjustable connector comprises a first portion attached to the pin, and a second portion, detachable from the first portion, attached to the transducer holder, and wherein the first and second portions are connected by a non-rotatable joint wherein one of the first and second portions contains a male element of D-shaped cross section and the other portion contains a corresponding female element of D-shaped cross section.

* * * * *